(12) United States Patent
Deckman et al.

(10) Patent No.: US 9,217,740 B2
(45) Date of Patent: Dec. 22, 2015

(54) ISOLATION AND CHARACTERIZATION OF A SINGLE MITOCHONDRION

(75) Inventors: Koren Holland Deckman, Gettysburg, PA (US); Barbara C. Levin, Gaithersburg, MD (US); Kristian Helmerson, Gaithersburg, MD (US); Rani B. Kishore, Gaithersburg, MD (US); Joseph E. Reiner, Gaithersburg, MD (US)

(73) Assignee: Gettysburg College, Gettysburg, PA (US)

( * ) Notice: Subject to any disclaimer, the term of this patent is extended or adjusted under 35 U.S.C. 154(b) by 246 days.

(21) Appl. No.: 13/100,342

(22) Filed: May 4, 2011

(65) Prior Publication Data

US 2011/0281269 A1 Nov. 17, 2011

Related U.S. Application Data

(62) Division of application No. 12/038,313, filed on Feb. 27, 2008, now abandoned.

(60) Provisional application No. 60/891,777, filed on Feb. 27, 2007.

(51) Int. Cl.
*C12Q 1/68* (2006.01)
*C12P 19/34* (2006.01)
*G01N 33/50* (2006.01)

(52) U.S. Cl.
CPC ............ *G01N 33/5079* (2013.01); *C12Q 1/686* (2013.01); *C12Q 1/6869* (2013.01)

(58) Field of Classification Search
CPC . C12Q 1/6883; C12Q 1/6869; G01N 33/5079
See application file for complete search history.

(56) References Cited

U.S. PATENT DOCUMENTS

| 8,008,008 B2 * | 8/2011 | Parr et al. ..................... 435/6.12 |
| 2002/0037499 A1 | 3/2002 | Quake et al. |
| 2003/0021017 A1 | 1/2003 | Eijsackers et al. |
| 2003/0049717 A1 | 3/2003 | Vesey et al. |
| 2003/0235812 A1 * | 12/2003 | Anderson et al. ................. 435/4 |
| 2007/0243634 A1 | 10/2007 | Pamula et al. |

OTHER PUBLICATIONS

Kuroiwa et al. Optical isolation of individual mitochondria of Physarum polycephalum for PCR analysis. Protoplasma (1996) vol. 194, pp. 275-279.*
Micke et al. Laser-assisted cell microdissection using the PALM system. Meth. Molec. Biol. (2004) vol. 293, pp. 151-166.*
Jeffries et al., "Using Polarization-Shaped Optical Vortex Traps for Single-Cell Nanosurgery", Nano Letters (2007), 7, 2, 415-420.
He et al., "Selective Encapsulation of Single Cells and Subcellular Organelles into Picoliter- and Femtoliter-Volume Droplets", Anal. Chem (2005), 77, 1539-1544.
Wang et al., "Isolation of a Single Rice Chromosome by Optical Micromanipulation", Journal of Optics A (2004) PureAppl. Opt. 6, 89-93.
Liu et al., "Preparation of a Single Rice Chromosome for Construction of a DNA Library Using a Laser Microbeam Trap", Journal of Biotechnology 109 (2004) 217-226.
Legros et al., "Organization and Dynamics of Human Mitochondrial DNA", Journal of Cell Science (2004), 117, 2653-2662.
Levin et al., "Comparison of the complete mtDNA genome sequences of human cell lines—HL-60 and GM10742A—from individuals with pro-myelocytic leukemia and leber hereditary optic neuropathy, respectively, and the inclusion of HL-60 in the NIST human mitochondrial DNA standard reference material—SRM 2392-I", Mitochondrian (2003), 2, 387-400.
Cavelier et al., "Analysis of mtDNA Copy Number and Composition of Single Mitochondrial Particles Using Flow Cytometry and PCR", Experimental Cell Research (2000), 259, 79-85.
Collins et al., "Microinstrument grdient-force optical trap", Applied Optics, Optical Society of America, vol. 38, No. 28, pp. 6068-6070, Oct. 1, 1999.

* cited by examiner

*Primary Examiner* — Kenneth R. Horlick
*Assistant Examiner* — David Thomas
(74) *Attorney, Agent, or Firm* — McNees, Wallace & Nurick LLC

(57) ABSTRACT

A method for identifying mitochondrial heteroplasmy within eukaryotic cells is provided. This method includes means for isolating and capturing a single mitochondrion from at least one eukaryotic cell, wherein the means for isolating and capturing a single mitochondrion further includes optical tweezers or a similar optical technology; means for analyzing the isolated and captured mitochondrion, wherein the means for analyzing the isolated and captured mitochondrion further includes a DNA amplification system and a sequencing system for amplifying and sequencing DNA extracted from the mitochondrion; means for identifying at least one mitochondrial heteroplasmy of interest; and means for using the DNA amplification and DNA sequencing systems to determine the presence or absence of the mitochondrial heteroplasmy within the eukaryotic cell from which the mitochondrion was obtained.

17 Claims, 4 Drawing Sheets

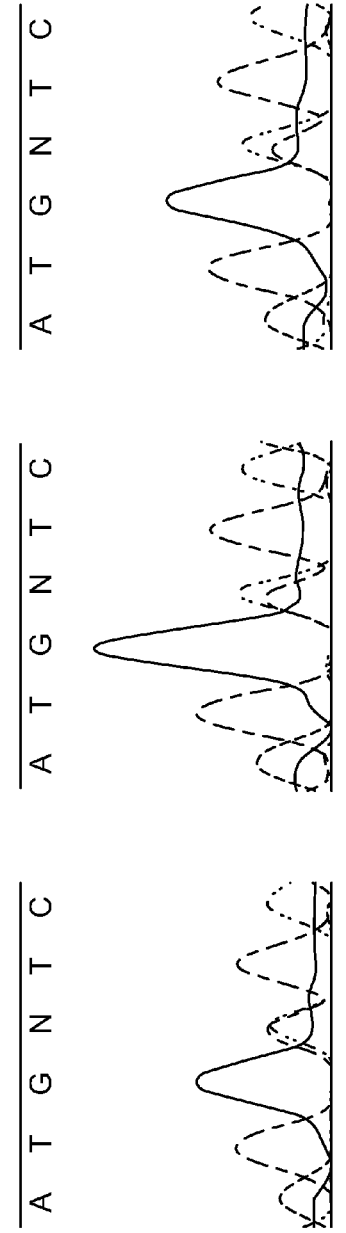
FIG. 4A Single Mitochondrion 1
FIG. 4B Single Mitochondrion 2
FIG. 4C Single Mitochondrion 3
FIG. 4D Single Mitochondrion 4
FIG. 4E Single Mitochondrion 6
FIG. 4F Single Cell 1

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acgaacgcac tcacagtcg                                                  19

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagcctctgt tgtcagattc ac                                              22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
catcataatc ctctctcaag g                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
```

```
aatctgatgt tttggttaaa c                                          21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caccctatta accactcacg                                            20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgagattagt agtatgggag                                            20
```

ISOLATION AND CHARACTERIZATION OF A SINGLE MITOCHONDRION

CROSS-REFERENCE TO RELATED APPLICATIONS

This patent application is a division of U.S. patent application Ser. No. 12/038,313 filed on Feb. 7, 2008 and entitled "Isolation and Characterization of a Single Mitochondrion", which claimed the benefit of U.S. Provisional Patent Application Ser. No. 60/891,777 filed on Feb. 27, 2007 and entitled "Isolation and Analysis of a Single Mitochondrion with Optical Tweezers", the disclosures of which are incorporated by reference herein in their entirety and made part of the present U.S. utility patent application for all purposes.

STATEMENT REGARDING FEDERALLY SPONSORED RESEARCH

This invention is related to work supported by the United States Government under Contract No. N0001406IP20022 awarded by the United States Office of Navy Research. The United States Government may have certain rights in this invention.

BACKGROUND OF THE INVENTION

The described invention relates in general to methods for studying biological systems, and more specifically to a system and method for isolating a single mitochondrion isolated from a eukaryotic cell for the primary purpose of identifying one or more specific mitochondrial heteroplasmies in the cell from which the mitochondria was obtained.

In cell biology, a mitochondrion (plural mitochondria) is a membrane-enclosed organelle found in most eukaryotic cells. These organelles are typically about 1-10 µm in size and are often described as "cellular power plants" because they generate most of the cell's supply of adenosine triphosphate (ATP), which is used as a source of chemical energy. In addition to supplying cellular energy, mitochondria are involved in a range of other processes, including signaling, cellular differentiation, cell death, as well as the control of the cell cycle and cell growth. Mitochondria have been implicated in several human diseases and may also play a role in the aging process. The number of mitochondria in a cell varies widely by organism and tissue type. Some cells may have only a single mitochondrion or very few mitochondria, whereas others can contain several thousand mitochondria. In humans, the mitochondria may contain about 615 distinct proteins, depending on the tissue of origin. Although most of a cell's DNA is contained in the cell nucleus, a mitochondrion has its own independent genome.

The human mitochondrial genome is a circular DNA molecule of about 16 kilobases. It encodes 37 genes: 13 for subunits of respiratory complexes I, III, IV, and V, 22 for mitochondrial tRNA, and 2 for rRNA. One mitochondrion can contain a variable number of copies of its DNA. As in prokaryotes, there is a very high proportion of coding DNA and an absence of repeats. Mitochondrial genes are transcribed as multigenic transcripts, which are cleaved and polyadenylated to yield mature mRNAs. Not all proteins necessary for mitochondrial function are encoded by the mitochondrial genome; most are coded by genes in the cell nucleus and imported to the mitochondrion. Thus, a mitochondrial disorder can be secondary to a mutation in either the nuclear DNA or in the mitochondrial DNA. The exact number of genes encoded by the nucleus and the mitochondrial genome differs between species.

The entire human mitochondrial DNA (mtDNA) sequence has been determined. See, e.g., Anderson, et al., "Sequence and organization of the human mitochondrial genome", Nature 290, 457 (1981); Andrews, et al., and "Reanalysis and revision of the Cambridge Reference Sequence for human mitochodrial DNA", Nature Genetics 23, 147 (1999). Mitochondrial genetics differ from nuclear (standard or Mendelian) genetics. Virtually all the mtDNA of a zygote is derived from the oocyte, and mtDNA disorders are transmitted by maternal inheritance. Maternal-linked (matrilineal) relatives presumably have identical mtDNA sequences, except perhaps at the site of a new mutation. Additionally, the mtDNA mutation rate is substantially higher than that of the nuclear DNA. Most cells contain dozens to thousands of mitochondria, and each mitochondrion contains several copies of mtDNA, resulting in high mtDNA copy number.

A wide variety of clinical manifestations are due to mutations in mitochondrial DNA, but are difficult to diagnose due to the varied clinical picture and the lack of sensitive or specific diagnostic testing. Past efforts to document mtDNA mutations in children believed to have mitochondrial disorders have been hampered by the size of the mitochondrial genome and the presence of numerous benign polymorphisms. Mitochondrial mutations can be single point mutations, or larger mutations deletions, insertions, rearrangements or duplications). Clinical mitochondrial dysfunction may be defined as idiopathic neuromuscular or multisystem disease, biochemical signs of energy depletion, and lack of another diagnosis. Mitochondrial disorders are evidenced when the cellular supply of energy is unable to keep up with demand and symptoms predominate in tissues with the highest energy requirements, such as brain and muscle. Mitochondrial disorders are most commonly displayed as neuromuscular disorders, including developmental delay, seizure disorders, hypotonia, skeletal muscle weakness and cardiomyopathy. Other manifestations which have been reported include gastroesophageal reflux, apnea, optic atrophy, deafness, acute liver failure, diabetes mellitus, and other hormonal deficiencies. Disorders such as MELAS (mitochondrial encephalomyopathy with lactic acidosis and stroke-like episodes), MERRF (myoclonic epilepsy with ragged-red fibers) and LHON (Leber's hereditary optic neuropathy) all result from single point mutations in the mtDNA genome.

Mammalian mitochondrial DNA (mtDNA) undergoes mutations at a higher rate than nuclear DNA. If all the mtDNA has the same mutation, the DNA is called homoplasmic; but a mixture of wild type and mutation is designated heteroplasmic. Thus, heteroplasmy is defined as the presence of a mixture of more than one type of an organellar genome (mitochondrial DNA or plastid DNA) within a cell or individual. The presence and degree of heteroplasmy is important in diagnostic medicine because heteroplasmies have been linked to mitochondrial-based diseases such as those listed above, which are maternally inherited. Since eukaryotic cells can contain hundreds of mitochondria with hundreds of copies of mtDNA, it is possible for single point mutations to affect only some of mitochondria and not others, thus giving rise to heteroplasmic mitochondrial genomes within a single individual.

Mitochondrial DNA (mtDNA) heteroplasmies are well documented at the multi-cell level; however, PCR and DNA sequencing (the recognized standard for determining the presence of heteroplasmy) can typically only distinguish heteroplasmy if it is present at least in 20% of the sample. The importance of detecting low frequency mutations is demonstrated by a number of cases in which a mother may not have a detectable mutation nor exhibit any symptoms of a mtDNA disease, yet her child does have the mutation and the mitochondrial DNA disease symptoms. In such cases, it is likely that the mutated genome copy number in the mother was too low to verify the presence of a mitochondrial DNA mutation using conventional methods. Most tissue studies in a typical genetic screening begin with millions of mitochondrial DNA copies as well as nuclear DNA, which adds to the overall complexity of the sample. By reducing the sample to a single mitochondrion and eliminating all other mitochondria and nuclear DNA, the mitochondrial DNA mutations found in a single mitochondrion will become detectable. Also, the detectable presence of heteroplasmy may differ depending on the type of tissue being examined meaning that not all tissue samples will yield consistent and reproducible results. Thus, there is a need for a sensitive and reliable method of testing a subject for risk of developing mitochondrial dysfunction or disease based on the presence or absence of mitochondrial heteroplasmy within their cells.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a system and method for characterizing a single mitochondrion is provided. This system includes optical means for isolating and capturing a single mitochondrion from a eukaryotic cell; and means for analyzing the isolated and captured mitochondrion, wherein the means for analyzing the isolated and captured mitochondrion typically includes a DNA amplification means and a DNA sequencing means.

In accordance with another aspect of the present invention, a system and method for identifying mitochondrial heteroplasmy within eukaryotic cells is provided. This system includes means for isolating and capturing a single mitochondrion from at least one eukaryotic cell, wherein the means for isolating and capturing a single mitochondrion further includes means for creating and operating optical tweezers or a comparable optical technology; means for analyzing the isolated and captured mitochondrion, wherein the means for analyzing the isolated and captured mitochondrion further includes a DNA amplification system and a sequencing system for amplifying and sequencing DNA extracted from the mitochondrion; means for identifying at least one mitochondrial heteroplasmy of interest; and means for using the DNA amplification and DNA sequencing systems to determine the presence or absence of the mitochondrial heteroplasmy within the eukaryotic cell from which the mitochondrion was obtained.

In yet another aspect of this invention, a system and method for characterizing a single mitochondrion is provided. This method includes providing at least one eukaryotic cell containing mitochondria; treating the at least one eukaryotic cell to release the cytoplasm therefrom, wherein the cytoplasm contains cellular organelles; isolating a single mitochondrion from the cellular organelles using optical tweezers or another optical technology; capturing the single mitochondrion isolated with the optical tweezers; treating the single mitochondrion to release mtDNA therefrom; selecting a target region within the mtDNA; amplifying the target region of the mtDNA; and sequencing the target region of the mtDNA to determine the nucleotide sequence thereof. The sequence of the target region is then compared to a known mitochondrial heteroplasmy for determining the presence or absence of the mitochondrial heteroplasmy within the eukaryotic cell and within the organism from which the cell was obtained.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the figures and associated descriptions are to be regarded as illustrative and not restrictive in nature.

BRIEF DESCRIPTION OF THE DRAWINGS

The accompanying figures, which are incorporated into and form a part of the specification, illustrate one or more exemplary embodiments of the invention and, together with the general description given above and detailed description given below, serve to explain the principles of the invention, and wherein:

FIGS. 4A-F provide DNA sequencing data obtained from a single mitochondrion.

DETAILED DESCRIPTION OF THE INVENTION

Figure 1:
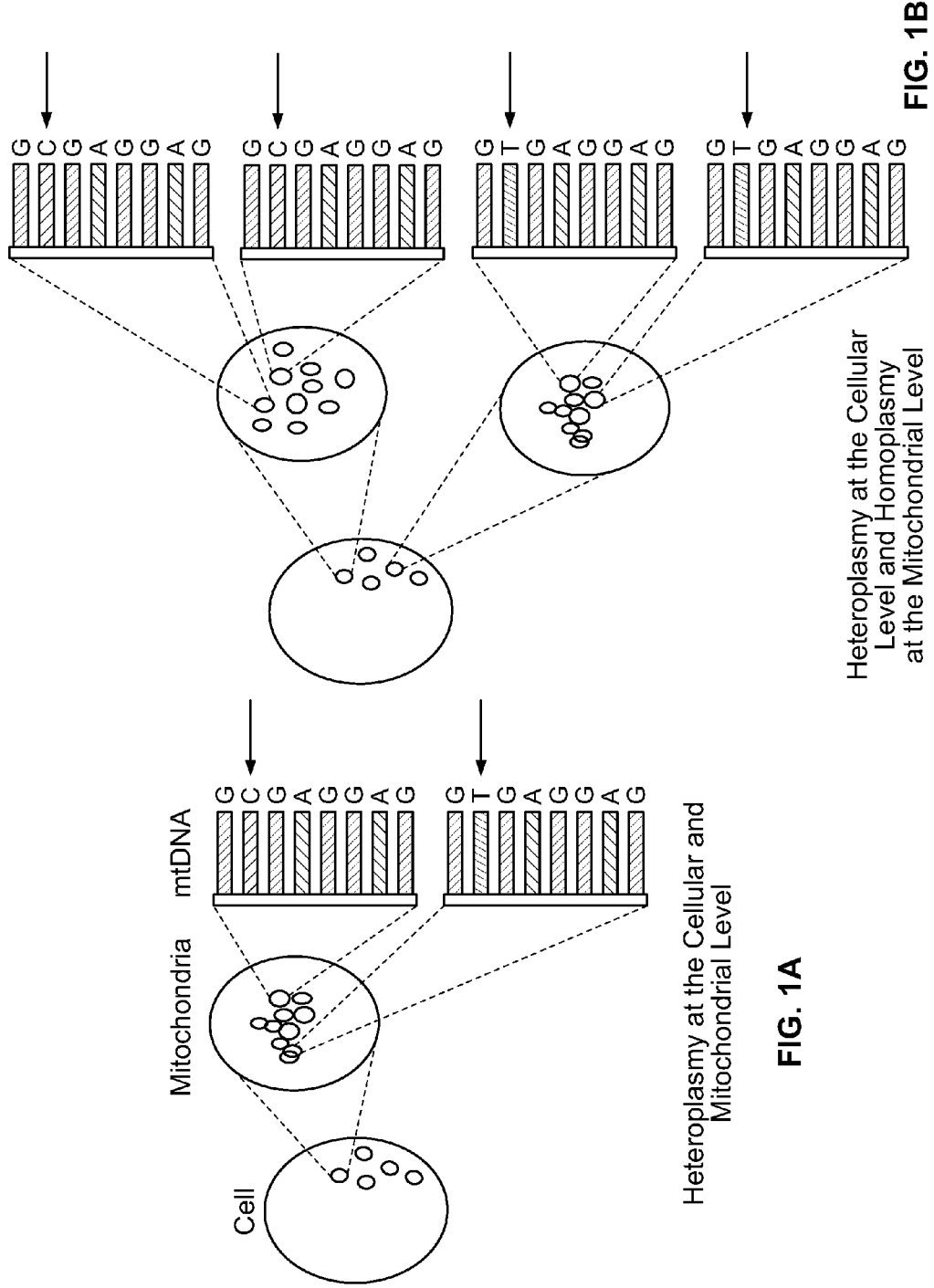
FIGS. 1A-B graphically illustrate the difference between a mtDNA heteroplasmy at the mitochondrial level and at the cellular level.

Exemplary embodiments of the present invention are now described with reference to the Figures. Reference numerals are used in the detailed description to refer to the various elements and structures. In other instances, well-known structures and devices are shown in block diagram form for purposes of simplifying the description. Although the following detailed description contains many specifics for the purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

In general terms, the present invention provides a system and method for isolating a single mitochondrion from the organelles found in the cytoplasm of a eukaryotic cell and amplifying and sequencing a target region of DNA within the genome of the mitochondrion for identifying at least one specific mitochondrial heteroplasmy in the cell and/or organism from which the mitochondria was obtained. As previously stated, an exemplary method of this invention includes the general steps of providing at least one eukaryotic cell containing mitochondria; treating the at least one eukaryotic cell to release the cytoplasm therefrom, wherein the cytoplasm contains cellular organelles; isolating a single mitochondrion from the cellular organelles using optical tweezers or another optical technology; capturing the single mitochondrion isolated with the optical tweezers; treating the single mitochondrion to extract mtDNA therefrom; selecting a target region within the mtDNA; amplifying the target region of the mtDNA; and sequencing the target region of the mtDNA to determine the nucleotide sequence thereof. The sequence of the target region is then compared to a known mitochondrial heteroplasmy for determining the presence or absence of the mitochondrial heteroplasmy within the eukaryotic cell and within the organism from which the cell was obtained. Having generally described this invention, a further understanding can be obtained by reference to a specific example detailed below, which is provided for purposes of illustration only and is not intended to be all inclusive or limiting unless otherwise specified.

EXAMPLE

The HL-60 cell line was used for the set of experiments comprising this example. The HL-60 (Human promyelocytic leukemia cells) cell line is a leukemic cell line that has been used for laboratory research on how certain kinds of blood cells are formed. The cell line was derived from a 36-year-old woman with acute promyelocytic leukemia at the National Cancer Institute and provides a continuous source of human cells for studying the molecular events of myeloid differentiation and the effects of physiologic, pharmacologic, and virologic elements on this process. HL-60 cells, at the multicell level, contain a C/T heteroplasmy at np 12071 (Levin, et al., *Mitochondrion* 2, 387-400 (2003)). The ratio of the wild type genome to the mutant genome is approximately 50:50 at the multicell level. FIGS. 1A-B depict two possible types of heteroplasmic distribution, wherein FIG. 1A depicts a mtDNA heteroplasmy at the mitochondrial level and FIG. 1B depicts a mtDNA heteroplasmy at the cellular level. The arrows indicate the location of the genetic mutation.

HL-60 cells (ATCC CCL-240) were maintained in liquid culture plates at 37° C., 5% $CO_2$ and moisture in a growth medium (10% fetal bovine serum, 100 u/mL penicillin G, 100 μg/mL streptomycin sulfate and 0.25 μg/mL amphotericin B in RPMI-1640M without glutamine). To acquire single mitochondria for amplification and sequencing, one mL of this culture was pelleted (14,000 RPM centrifugation, 1 min), and the pellet was resuspended in 1 mL growth medium (RPMI-1640 described above) containing 0.1 μM Mitotracker Green FM (Invitrogen, Inc.) in DMSO. The cells were incubated (37° C., 15 min), pelleted again, and washed (2×1 mL fresh growth media). Cells were resuspended in 1 mL fresh growth media at an appropriate dilution and stored at 4° C. in preparation for optical tweezers extraction.

Figure 2:
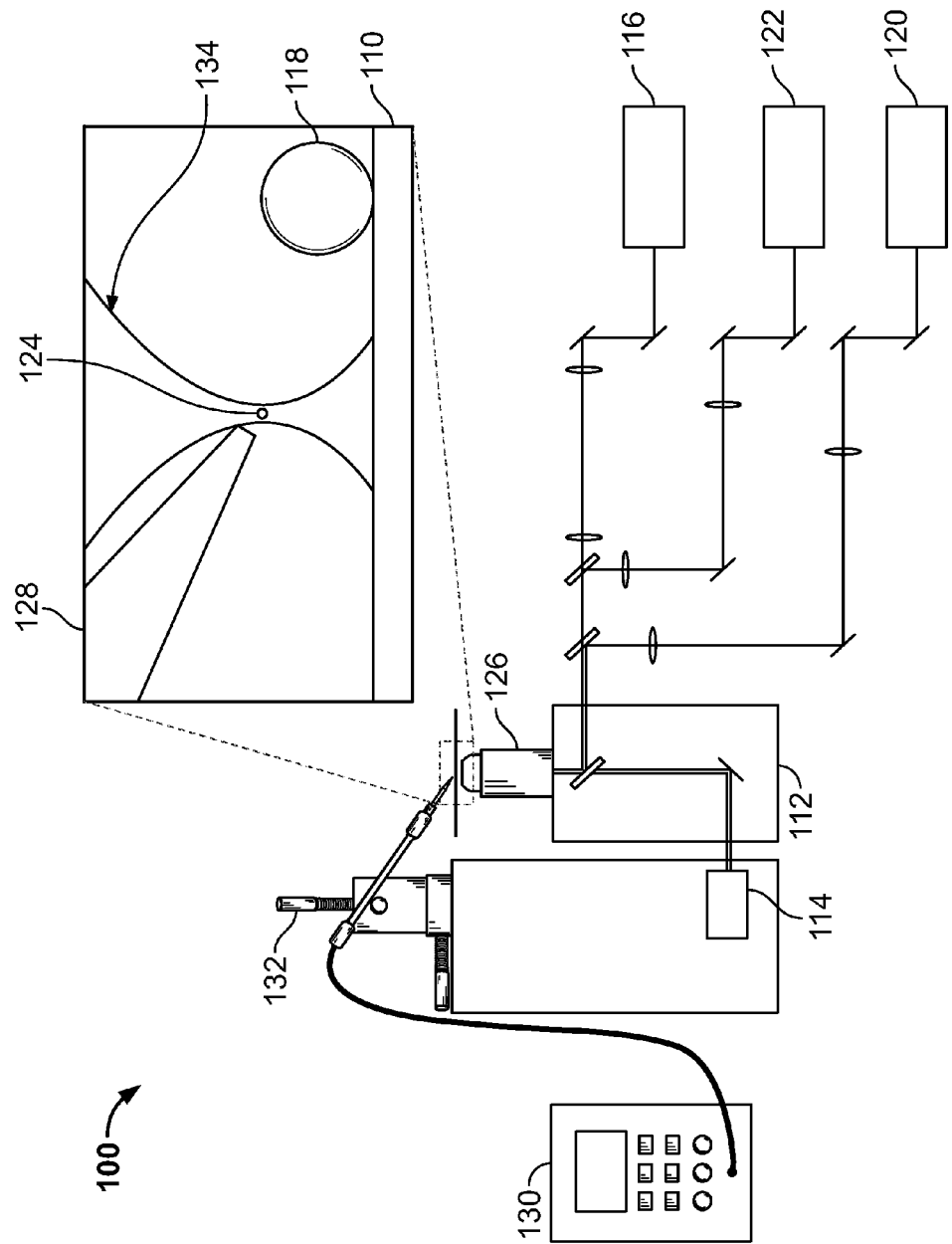
FIG. 2 is an illustration of an exemplary optical capture system.
Figure 3A:
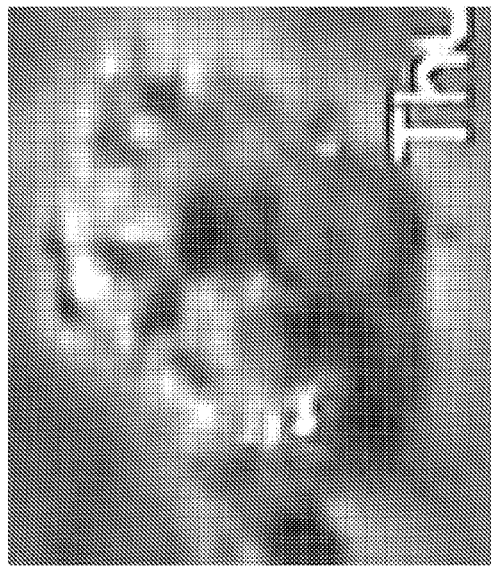
FIGS. 3A-D are a series of photographic images of an exemplary mitochondrion isolation and capture process in accordance with to the present invention.
Figure 3B:
Figure 3C:
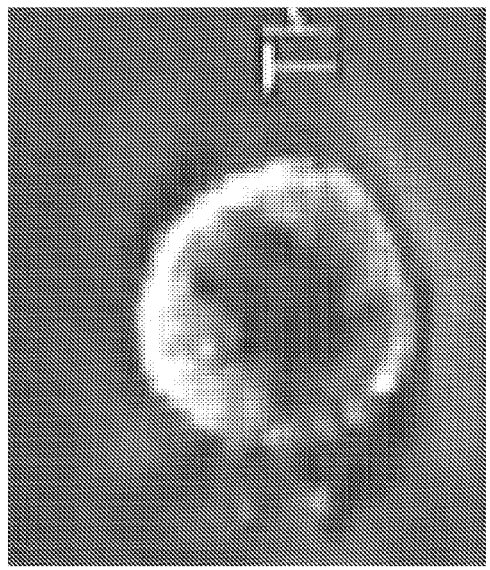
Figure 3D:

With reference now to FIG. 2, a 120 μL well was created by mounting a #0 coverslip to a microscope slide 110 containing a 1 cm hole by using vacuum silicone grease. A 10 μL sample of the prepared HL-60 culture was mixed with 110 μL of PBS buffer (137 mM NaCl, 10 mM sodium phosphate, 2.7 mM KCl, pH 7.2), and the solution was pipetted in the well. The cells in solution were allowed to settle down onto the glass cover slip. The cell concentration after settling was typically about 1 cell per 1 mm². An inverted microscope 112 (Axiovert 100, Carl Zeiss) was used to view the contents of the slide; once the cells settled, a CCD camera 114 was used to visualize the fluorescence of mitochondria stained with Mitotracker Green excited by an $Ar^+$ laser 116 at 488 nm. Individual cells 118 were lysed with a pulsed (5 ns) UV laser 120 at 355 nm. A 500 mW infrared laser 122 at 1064 nm (IPG Photonics) was used to optically trap each mitochondrion particle 124, which was identified by fluorescence excitation. FIG. 2 graphically depicts an exemplary system 100 for isolating and capturing a single mitochondrion 124 wherein an $Ar^+$ laser 116 tuned to the 488 nm line (fluorescence), a 1064 nm ND:YAG fiber laser (trap) 122, and a 355 nm (UV) frequency tripled ND:YAG pulse laser 120 are all coupled into the back aperture of a 100×NA 1.4 oil-immersion objective 126. To acquire a single mitochondrion particle 124 for genotyping analysis, a femtopipette tip 128 (Eppendorf, Inc.) with an attached pump 130 (Femtojet, Eppendorf, Inc.) was positioned less than 1 micron from the trapped mitochondrion 124 with a micromanipulator 132 and positive pressure was first applied to prevent capillary action. The positive pressure was then reduced as the optical tweezers 134 were shuttered to draw the mitochondrion up into the tip 128. The contents of the Femtotip 128 were transferred into a 250 μL PCR tube containing 10 μL dd$H_2O$ using positive pressure. The end of the Femtotip 128 in this process was broken and only this end fragment was carried with the PCR tube and sample. FIGS. 3A-D are images from a video sequence of the mitochondrion capture process. FIG. 3A shows an HL-60 cell; FIG. 3B shows a lysed HL-60 cell; FIG. 3C shows a single mitochondrion (arrow) trapped and near a micropipette; and FIG. 3D shows the mitochondrion (arrow) inside the tip of the micropipette.

Each sample consisting of the end piece of the Femtotip and its single mitochondrion was sonicated (Branson Sonifier 450) with 2 second pulses for 2 minutes at 30% intensity. Heat (95° C., 10 min) was used to further lyse the mitochondrion. Mitochondrial DNA was then subjected to three rounds of PCR using 0.4 mM of each of the four deoxynucleotides (dATP, dCTP, dTTP and dGTP) and 2.5 units Taq DNA polymerase following the manufacturer's protocol (GoTaq reagent, Promega, Inc.). The PCR amplicons were purified after each 35 cycle program using QIAquick columns (Qiagen, Inc.) according to the manufacturer's protocol. The amplicon was eluted with dd$H_2O$. One to 5 μL of the amplicon was used in the subsequent PCR amplifications. The volume was dependent upon the success of the amplification reaction as visualized by agarose gel electrophoresis (see below). Exemplary primer sequences are shown in Table 1.

TABLE 1

PCR primer information.

| Primer | Nucleotide Position* | Sequence |
|---|---|---|
| 1F | 11760 | 5' ACGAACGCACTCACAGTCG 3' (SEQ ID NO: 1) |
| 1R | 12189 | 5' AAGCCTCTGTTGTCAGATTCAC 3' (SEQ ID NO: 2) |
| 2F | 11779 | 5' CATCATAATCCTCTCTCAAGG 3' (SEQ ID NO: 3) |
| 2R | 12176 | 5' AATCTGATGTTTTGGTTAAAC 3' (SEQ ID NO: 4) |
| 3F | 15 | 5' CACCCTATTAACCACTCACG 3' (SEQ ID NO: 5) |
| 3R | 484 | 5' TGAGATTAGTAGTATGGGAG 3' (SEQ ID NO: 6) |

All positive PCR amplification controls contained the appropriate primer set and 1.6 ng HL-60 total DNA (ATCC-CCL 240D). All PCR negative controls contained the appropriate primer set but lacked any amplifiable DNA. A thermocycler (9700 or 2400, Perkin Elmer Inc.) 140 was used in all PCR amplifications. Typical PCR parameters were: 95° C. for 10 min, 35 cycles (94° C. for 20 sec, 50° C. for 20 sec, 72° C. for 40 sec), and 72° C. for 7 mins. All PCR reactions were analyzed with 2% agarose gels in TBE (100 mM Tris, 90 mM boric acid and 1 mM EDTA, pH 8.3) and stained with 0.5 μg/mL ethidium bromide.

Sequencing system 150 was utilized by mixing 1 µl of the final purified amplicon from a single mitochondrion with 0.5 µM 1F, 2F or 3F (depending on which primer set was used for amplification in round 3) and 8 µl BigDye Terminator v1.1 Cycle Sequencing Kit (Applied Biosystems, Inc.) according to the manufacturers protocol. Sequencing reactions were conducted using the following thermocycler parameters: 25 cycles of 96° C. for 15 sec, 50° C. for 5 sec, and 60° C. for 2 min; hold at 4° C. Products were purified using the Performa DTR gel cartridge (Edge Biosystems) eluted with 20 µl ddH$_2$O, and dried in a vacuum microcentrifuge (SpeedVac, Sorvall, Inc.) for 1.5-2 hours at medium heat. Twenty µL of Template Suppression Reagent (Applied Biosystems, Inc.) or formamide was added to each sample and separated by capillary gel electrophoresis (310 Genetic Analyzer, Applied Biosystems, Inc.). Sequence Navigator v1.0.1 (Applied Biosystems, Inc.) was used for sequence alignment.

The sequences of individual amplicons from single mitochondria are shown in FIG. 4A-E. FIG. 4A shows the presence of a heteroplasmy (located at position 12071) at the single mitochondrial level with approximate equal abundance of T and C. FIG. 4B-C show the presence of a heteroplasmy at the single mitochondrial level with C being more abundant. FIG. 4D-E show a heteroplasmy with T being more predominant. These results demonstrate that heteroplasmy exists at the mitochondrial level. FIG. 4F represents the heteroplasmy as sequenced from single cells which where isolated using optical tweezers and analyzed according to the system and methods of the present invention.

While the present invention has been illustrated by the description of exemplary embodiments thereof, and while the embodiments have been described in certain detail, it is not the intention of the Applicant to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the applicant's general inventive concept.

---

What is claimed:

1. A method for identifying a mitochondrial heteroplasmy, comprising:
   (a) providing at least one eukaryotic cell, wherein the cytoplasm of the at least one eukaryotic cell contains mitochondria, wherein the mitochondria contains mitochondrial DNA, and wherein the mitochondrial DNA is heteroplasmic;
   (b) lysing the at least one eukaryotic cell with a laser to release the cytoplasm and mitochondria therefrom;
   (c) isolating and capturing a single mitochondrion from the mitochondria in the cellular cytoplasm released from the at least one eukaryotic cell with optical tweezers;
   (d) acquiring the single mitochondrion with a femtopipette tip having a pump attached thereto;
   (e) sonicating and then heating the single mitochondrion with a sonicator and a heat source to release the mitochondrial DNA from the single mitochondrion;
   (f) providing a series of primers, wherein the primers are specific to pre-selected target regions of the mitochondrial DNA;
   (g) amplifying the pre-selected target regions of the mitochondrial DNA by polymerase chain reaction;
   (h) determining the nucleotide sequence of each amplified target region with a sequencing system;
   (i) comparing the nucleotide sequence of each amplified target region to sequences of mitochondrial DNA that represent known mitochondrial heteroplasmies associated with specific disease states or health conditions of interest; and
   (j) identifying the presence of a specific mitochondrial heteroplasmy within the single isolated mitochondria based on the comparison of the amplified target region to the sequences of mitochondrial DNA that represent known mitochondrial heteroplasmies.

2. The method of claim 1, wherein the at least one eukaryotic cell is a mammalian cell.

3. The method of claim 1, wherein the laser for lysing the at least one eukaryotic cell to release the cytoplasm and mitochondria therefrom is a pulsed 5 ns UV laser.

4. The method of claim 1, wherein the optical tweezers further include a 1064 nm Nd:YAG fiber laser operating at about 1064 nm with about 1 W of power.

5. The method of claim 1, wherein the primers include the nucleotide sequences set forth in SEQ ID NO: 1 and SEQ ID NO: 2.

6. The method of claim 1, wherein the primers include the nucleotide sequences set forth in SEQ ID NO: 3 and SEQ ID NO: 4.

7. The method of claim 1, wherein the primers include the nucleotide sequences set forth in SEQ ID NO: 5 and SEQ ID NO: 6.

8. A method for identifying mitochondrial heteroplasmy, comprising:
   (a) capturing at least one eukaryotic cell, wherein the cytoplasm of the at least one eukaryotic cell contains mitochondria, wherein the mitochondria contains mitochondrial DNA, and wherein the mitochondrial DNA is heteroplasmic;
   (b) using a laser to lyse the at least one eukaryotic cell to release the cytoplasm and mitochondria therefrom;
   (c) using optical tweezers to isolate and capture a single mitochondrion from the mitochondria in the cellular cytoplasm released from the at least one eukaryotic cell;
   (d) using a femtopipette tip having a pump attached thereto to acquire the single mitochondrion;
   (e) using a sonicator and then a heat source, wherein the sonicator and the heat source are operative to release the mitochondrial DNA from the single mitochondrion;
   (f) using a series of primers to amplify target regions of the mitochondrial DNA using polymerase chain reaction; and
   (g) using sequencing to determine the nucleotide sequence of each amplified target region, and
   (h) comparing the nucleotide sequence of each amplified target region to sequences of mitochondrial DNA that represent known mitochondrial heteroplasmies associated with specific disease states or health conditions of interest; and
   (i) identifying the presence of a specific mitochondrial heteroplasmy within the single isolated mitochondria based on the comparison of the amplified target region to the sequences of mitochondrial DNA that represent known mitochondrial heteroplasmies.

9. The method of claim 8, wherein the at least one eukaryotic cell is a mammalian cell.

10. The method of claim 8, wherein the laser for lysing the at least one eukaryotic cell to release the cytoplasm and mitochondria therefrom is a pulsed 5 ns UV laser.

11. The method of claim 8, wherein the optical tweezers further include a 1064 nm Nd:YAG fiber laser operating at about 1064 nm with about 1 W of power.

12. The method of claim 8, wherein the primers include the nucleotide sequences set forth in SEQ ID NO: 1 and SEQ ID NO: 2.

13. The method of claim 8, wherein the primers include the nucleotide sequences set forth in SEQ ID NO: 3 and SEQ ID NO: 4.

14. The method of claim 8, wherein the primers include the nucleotide sequences set forth in SEQ ID NO: 5 and SEQ ID NO: 6.

15. The method of claim 8, further comprising the step of labeling the mitochondria with a fluorescent dye.

16. The method of claim 8, wherein the target region includes at least one mutation in the mitochondrial DNA, and wherein the at least one mutation is associated with at least one disease state or condition of interest.

17. The method of claim 8, wherein amplifying the target region of DNA further includes the use of polymerase chain reaction.

* * * * *